United States Patent [19]

Yamasaki

[11] Patent Number: 5,152,283

[45] Date of Patent: Oct. 6, 1992

[54] RESUSCITATOR TUBE WITH MOUTHPIECE SEALING MEANS

[76] Inventor: Robert N. Yamasaki, 1354 Trouville Ave. #A, Grover City, Calif. 93433

[21] Appl. No.: 685,424

[22] Filed: Apr. 15, 1991

[51] Int. Cl.⁵ .................... A61M 16/00; A62B 7/00; A62B 18/02; A62B 9/06
[52] U.S. Cl. .................. 128/202.28; 128/207.14; 128/204.18; 128/205.25
[58] Field of Search ............ 128/202.28, 202.29, 128/203.11, 207.14, 911, 205.25, 206.16, 206.24, 204.18

[56] References Cited

U.S. PATENT DOCUMENTS

| 2,318,790 | 5/1943 | Martindale et al. | 128/206.16 |
| 2,887,105 | 5/1959 | Brown et al. | 128/203.11 |
| 3,021,836 | 2/1962 | Marsden | 128/202.28 |
| 3,037,497 | 6/1962 | Roberson | 128/202.29 |
| 3,057,347 | 10/1962 | McGee | 128/202.28 |
| 3,124,124 | 3/1964 | Cross | 128/203.11 |
| 3,518,989 | 7/1970 | Seeler | 128/203.11 |
| 4,535,765 | 8/1985 | Paoluccio et al. | 128/203.11 |

FOREIGN PATENT DOCUMENTS

| 793601 | 9/1968 | Canada | 128/202.28 |
| 1156121 | 11/1983 | Canada | 128/202.28 |
| 1373685 | 8/1964 | France | 128/202.28 |
| 901357 | 7/1962 | United Kingdom | 128/202.28 |

Primary Examiner—Edgar S. Burr
Assistant Examiner—Kimberly L. Asher
Attorney, Agent, or Firm—Leon Gilden

[57] ABSTRACT

A simple and inexpensive resuscitator tube for applying mouth to mouth resuscitation includes a one piece hollow tubular member having mouthpieces affixed to each end. A plurality of openings at a lower end of the tube shields a victim and rescuer from regurgitated and exhaled material.

1 Claim, 4 Drawing Sheets

PRIOR ART

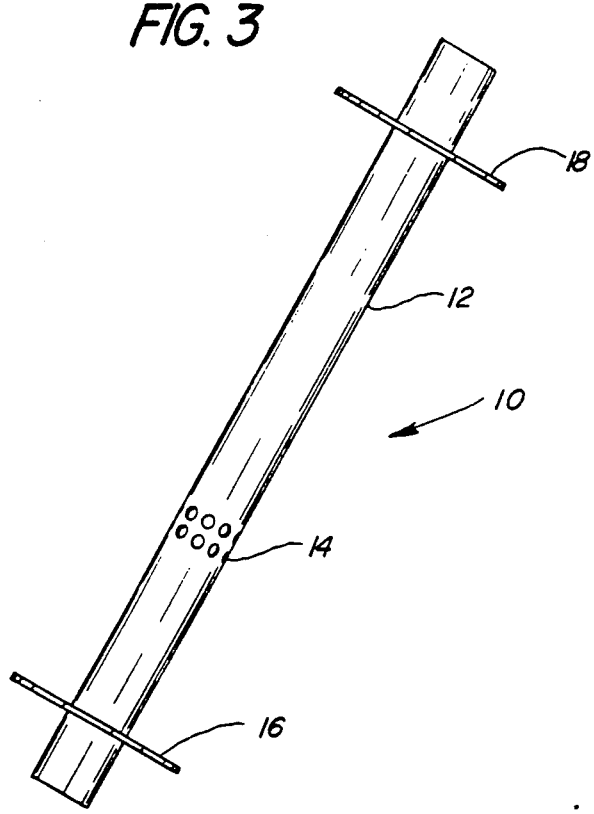

RESUSCITATOR TUBE WITH MOUTHPIECE SEALING MEANS

BACKGROUND OF THE INVENTION

1. Field of the Invention

The present invention relates to devices for facilitating the administration of mouth to mouth resuscitation. More particularly, the present invention relates to resuscitators which provide shielding from regurgitated and exhaled material.

2. Description of the Prior Art

The use of resuscitators is known in the prior art. More specifically, U.S. Pat. No. 3,080,864, which issued to Robert A. Berman on Mar. 12, 1963, discloses a mouth to mouth resuscitator that particularly relates to a resuscitator which is made of plastic material. U.S. Pat. No. 3,106,916, which issued to Daniel N. Matthes on Oct. 15, 1963, discloses a resuscitation tube which serves to introduce air into the mouth of a person needing artificial respiration. This latter tube is strengthened in the area receivable into a patient's mouth and an associated shield is slidable on a stiffened portion of the tube to seal against either an exterior or interior portion of the victim's lips. U.S. Pat. No. 3,303,854, which issued to William J. Detmer, III and Gordon P. St. Clair on Feb. 14, 1967, discloses a mouth to mouth resuscitator having a tubular mouthpiece providing an unobstructed opening longitudinally and having a smooth unobstructed exterior of substantially uniform diameter along a full length thereof. U.S. Pat. No. 3,407,810, which issued to Lester L. Waldrep on Oct. 29, 1968, discloses a tube for use in mouth to mouth resuscitation having a saliva trap at the victim's end and offset mouthpieces. U.S. Pat. No. 3,802,428, which issued to Melvin J. Sherman on Apr. 9, 1974, discloses a disposable device for applying mouth to mouth resuscitation comprising a prophylactic face mask portion for the person applying artificial respiration and a tubular member for channeling air into the mouth of the victim to be revived, while preventing reverse flow of fluids and air expelled or inhaled by the victim.

While the above mentioned devices are each suitable for their intended usage, none of these devices disclose a resuscitator tube that can easily shield a victim and his rescuer from regurgitation and exhaled material. Therefore, it can be appreciated that there exists a continuing need for new and improved resuscitator tubes which can be employed to shield a victim and rescuer from regurgitated and exhaled material. In this regard, the present invention substantially fulfills this need.

SUMMARY OF THE INVENTION

In view of the foregoing disadvantages inherent in the known types of resuscitator tubes now present in the prior art, the present invention provides an improved resuscitator tube construction wherein the same can be used to shield a victim and rescuer from regurgitated and exhaled material. As such, the general purpose of the present invention, which will be described subsequently in greater detail, is to provide a new and improved resuscitator tube which has all the advantages of the prior art resuscitator tubes and none of the disadvantages.

To attain this, the present invention comprises a simple and inexpensive resuscitator tube for applying mouth to mouth resuscitation which includes a one piece hollow tubular member having mouthpieces affixed to each end. A plurality of openings at the lower end of the tube shields a victim and rescuer from regurgitated and exhaled material.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved resuscitator tube which has all the advantages of the prior art resuscitator tubes and none of the disadvantages.

It is another object of the present invention to provide a new and improved resuscitator tube which may be easily and efficiently manufactured and marketed.

It is a further object of the present invention to provide a new and improved resuscitator tube which is of a durable and reliable construction.

An even further object of the present invention is to provide a new and improved resuscitator tube which is susceptible of a low cost of manufacture with regard to both materials and labor, and which accordingly is then susceptible of low prices of sale to the consuming public, thereby making such resuscitator tubes economically available to the buying public.

Still yet another object of the present invention is to provide a new and improved resuscitator tube which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a side elevation view of the resuscitator tube comprising the present invention.

FIG. 4 is a perspective view of the present invention showing it in use.

DESCRIPTION OF THE PREFERRED EMBODIMENT

Figure 1:
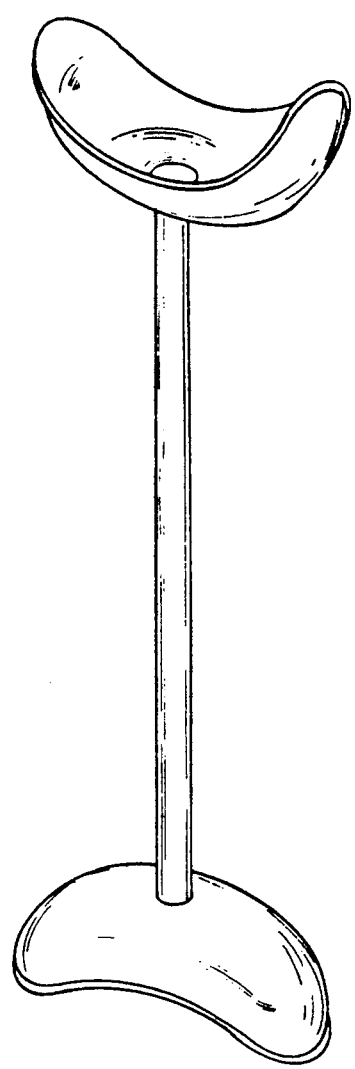
FIG. 1 is a side perspective view of a known prior art mouth to mouth resuscitator.

With reference now to the drawings, and in particular to FIGS. 3 and 4 thereof, a new and improved resuscitator tube embodying the principles and concepts of the present invention and generally designated by the reference numeral 10 will be described.

Figure 2:
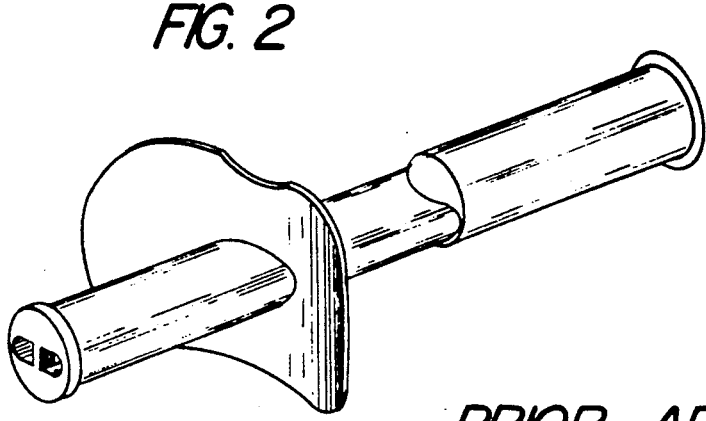
FIG. 2 is a perspective view of a known prior art resuscitator tube.

Initially, however, reference is made to FIGS. 1 and 2 of the drawings wherein typical prior art resuscitator tubes are illustrated. The majority of prior art devices comprise some means for maintaining separation between a rescuer and a victim. The mouth to mouth resuscitator tube of FIG. 1 is of the type shown in U.S. Pat. No. 3,080,064 which issued to Robert A. Berman on Mar. 12, 1963. This device provides a rigid tube extending between two flexible mouthpieces which fit over and cover the lower face portion of the victim and rescuer. The resuscitator tube of FIG. 2 is of the type shown in U.S. Pat. No. 3,106,916 which issued to Daniel N. Matthes on Oct. 15, 1963. This device, also common in the prior art, features a rigid tube extending between a mouthpiece for the operator and a terminal portion which engages the victim's mouth.

Devices exist which include a provision for preventing backstreaming of regurgitated and exhaled material by incorporating unidirectional valves of various construction into a rigid tube. The relative sophistication of the valves increases the cost, reduces the reliability and increases the amount of time required to maintain the device. The present invention, on the other hand, is designed to provide a simple, inexpensive resuscitator tube which fulfills the purposes of prior art inventions, i.e., pressurize and inflate a victim's lungs, and shield a rescuer and victim from regurgitated material.

A first embodiment of the resuscitator tube 10 is illustrated in FIGS. 3 and 4. The device 10 is of a very simple construction and consists of a one piece hollow tubular member 12 having a generally cylindrical shape with the same cross section extending the full length of the member. The lower end of the tubular member 12 which is considered to be the victim's end, includes a plurality of openings 14. The openings 14 are designed to allow regurgitated and exhaled materials to exit the tubular member 12, thus preventing the material from backstreaming into the victim's mouth or continuing upstream to the rescuer's mouth.

Referring again to FIGS. 3 and 4, a mouthpiece 16 is affixed to the lower (victim's) end of the tubular member 14 and is adapted to sealingly engage the mouth of the victim so that substantially all of the air blown from the mouth of the rescuer will pass into the mouth and to the lungs of the victim. In a similar fashion, a mouthpiece 18 is affixed to the upper (rescuer's) end of the tubular member 14 and forms a seal between the lips of the rescuer and the respective end of the tube. Sealing ensures that substantially all of the air blown from the rescuer will pass into the tubular member 12.

In use then, a rescuer inserts the lower end of the tubular member 12 between the lips and teeth of the victim as shown in FIG. 4. Mouthpiece 16 is held against the lips of the victim by light pressure on the tubular member 12. The rescuer's hand is positioned in such a way that his fingers can cover the plurality of openings 14 in the tubular member 12. The nose of the victim is closed by finger pressure from the rescuer's other hand on the victim's nostrils. The rescuer then places his mouth over the upper end of tubular member 12 until the upper mouthpiece 18 makes contact with his lips, covers the plurality of opening 14 and blows through the tube with sufficient force to inflate the victim's lungs. The rescuer then removes his mouth from the tubular member 12 and releases his fingers from the openings 14 to allow the victim to exhale air or material. This operation is repeated several times a minute until the victim hopefully begins to breathe independently.

Figure 5:
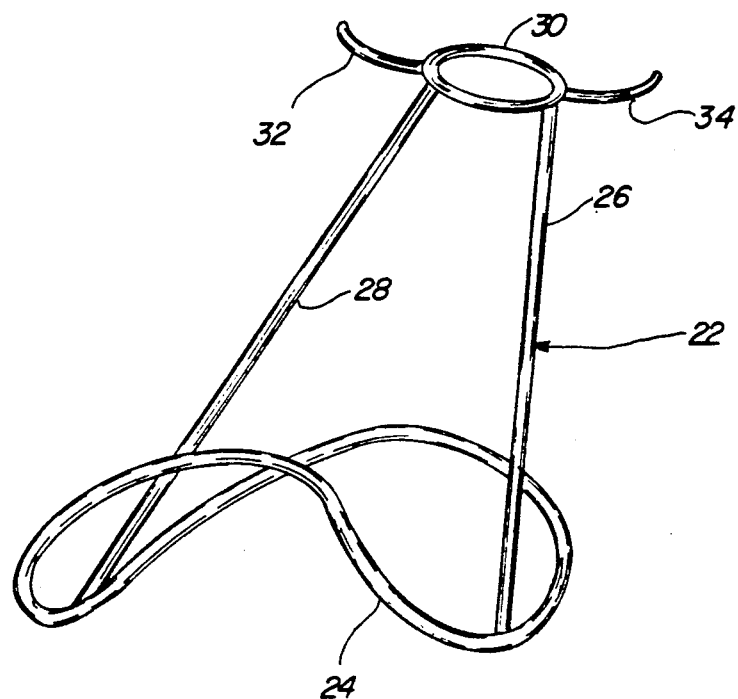
FIG. 5 is a perspective view of a tube holder associated with the present invention.
Figure 6:
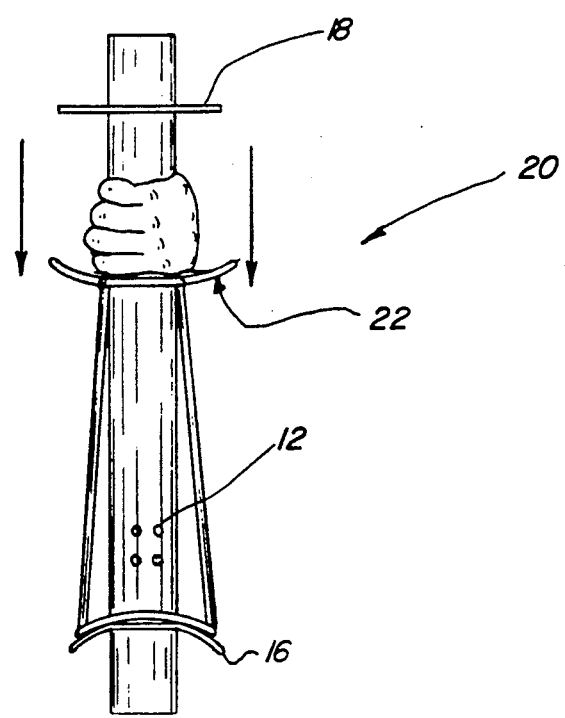
FIG. 6 is a perspective view of the present invention illustrating a use of the holder therewith.

FIGS. 5 and 6 of the drawings illustrate a modified embodiment of the tubular member wherein such modified embodiment is identified by the reference numeral 20. In this modified version of the tubular member 20, a wire member 22 is provided to improve the sealing characteristics of the lower mouthpiece 16.

As best shown in FIG. 5, wire member 22 consists of a flexible curvilinearly-shaped lower section 24 and a more rigid upper section defined by a pair of wire members 26, 28, both of which are attached at their lower ends in an integral manner to the lower section 24. The upper ends of the wire members 26, 28 are integrally or otherwise fixedly secured to a circular wire member 30. Additionally, a pair of oppositely disposed hand supports are defined by outwardly extending wire members 32, 34 which are also fixedly secured to the circular wire member 30.

Figure 7:
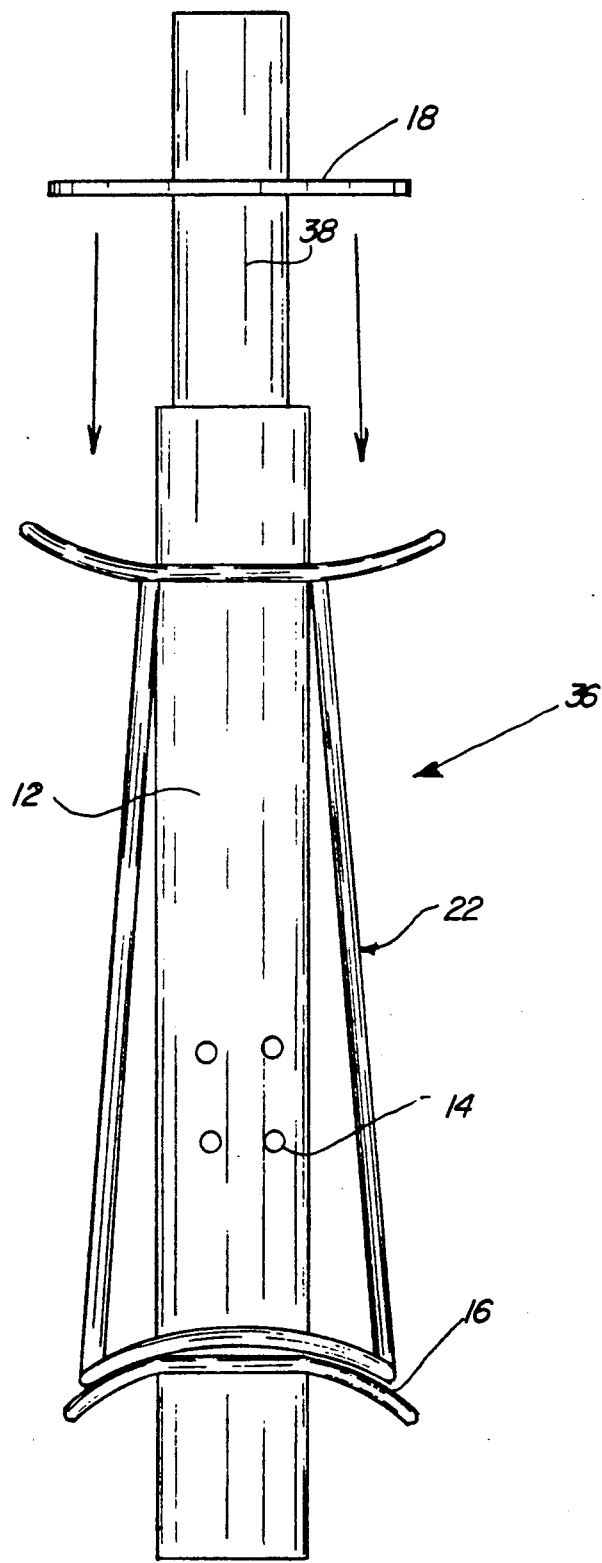
FIG. 7 is a front elevation view further illustrating a use of the holder and tube together.

During a use thereof, the wire member 22 is slidably permanently attached to the tubular member 14 as best illustrated in FIG. 6. In this regard, the wire member 22 would be positioned over the tubular member 14 prior to a permanent installation of the lip guard 18, with the tube 14 then being slidably positionable through the ring wire member 30. During an operation of the modified embodiment 20, the mouthpiece 16 is pressed against a victim's lips by application of a downward pressure provided by a rescuer. This downward pressure is accomplished by the rescuer positioning his hand around the tube 14 and resting it upon the hand supports, 32, 34. The flexible lower section 24 of the wire member 22 effects a curvilinear bending of the mouthpiece 16 whereby the mouthpiece forms to the shape of the victim's face, thereby providing an airtight seal for efficient dispersal of air into the victim's lungs. In this connection, the wire members 26, 28 can be flexibly bent inwardly or outwardly as desired to effect the desired curvilinear shape of the member 24, thereby to achieve the best possible airtight positioning of the mouthpiece 16. FIG. 7 illustrates a final envisioned embodiment of the present invention which is generally designated by the reference numeral 36. This final embodiment of the invention also utilizes an air delivery tube 12 having apertures 14 and oppositely disposed mouthpieces 16, 18. A wire member 22 is also provided for controlling the shape of the mouthpiece 16 during a use of this modified embodiment 36 of the invention. However, an improvement is provided in this embodiment 36 through the use of a further tube 38 which is slidably positioned within the air tube 12 with the mouthpiece 18 then being fixedly secured to this additional air tube. The air tube 38 is telescopingly moveable within the tube 12 to thus facilitate an adjustable lengthening or shortening of the invention 36 so as to provide an improved operation thereof. The manner and usage of operation of this final embodiment 36 of the invention is quite apparent and no further discussion relative thereto will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A resuscitator assembly comprising:
   a one-piece hollow tubular member having an upper end, a lower end, and an outer surface;
   an upper rescuer mouthpiece;
   a lower victim mouthpiece having an upper surface and a lower victim contacting surface;
   a plurality of openings in said lower end of said tubular member proximate said victim mouthpiece;
   means for sealing said victim mouthpiece to the face of the victim during resuscitation, said means for sealing comprising a wire member having an upper ring member with a plurality of hand supports extending outwardly therefrom, a lower ring member which engages said upper surface of said victim mouthpiece, and a plurality of connecting members fixedly secured at upper ends to said upper ring member and at lower ends to said lower ring member;
   said wire member slidably located on said outer surface of said tubular member;
   wherein during resuscitation the rescuer's hand exerts a downward sealing force on said victim mouthpiece via said upper ring, said hand supports, said connecting member, and said victim mouthpiece-engaging lower ring member.

* * * * *